(12) United States Patent
Martin et al.

(10) Patent No.: US 8,757,004 B2
(45) Date of Patent: Jun. 24, 2014

(54) GRIP MOUNTED SAFETY SHIELD

(75) Inventors: Paulo A. Martin, Somerset, MA (US);
James B. Smallwood, Milton, MA (US);
Edward A. McHenry, Jr., Holbrook, MA (US)

(73) Assignee: Illinois Tool Works Inc., Glenview, IL (US)

( * ) Notice: Subject to any disclaimer, the term of this patent is extended or adjusted under 35 U.S.C. 154(b) by 396 days.

(21) Appl. No.: 13/262,142

(22) PCT Filed: Feb. 26, 2010

(86) PCT No.: PCT/US2010/025609
§ 371 (c)(1),
(2), (4) Date: Jan. 3, 2012

(87) PCT Pub. No.: WO2010/117514
PCT Pub. Date: Oct. 14, 2010

(65) Prior Publication Data
US 2012/0111123 A1    May 10, 2012

Related U.S. Application Data

(60) Provisional application No. 61/165,207, filed on Mar. 31, 2009.

(51) Int. Cl.
*G01N 3/02*        (2006.01)

(52) U.S. Cl.
USPC ............................................. 73/856; 73/860

(58) Field of Classification Search
USPC ............................. 73/856–860, 760, 865–860
See application file for complete search history.

(56) References Cited

U.S. PATENT DOCUMENTS

| | | | | |
|---|---|---|---|---|
| 3,999,340 A | * | 12/1976 | Bogese et al. | 52/147 |
| 4,537,080 A | | 8/1985 | Christiansen | |
| 4,738,126 A | * | 4/1988 | Haberle | 70/14 |
| 4,866,992 A | * | 9/1989 | Rice et al. | 73/856 |
| 5,095,757 A | * | 3/1992 | Larsen et al. | 73/857 |
| 5,431,062 A | * | 7/1995 | Baratta | 73/856 |
| 5,528,942 A | * | 6/1996 | Baratta | 73/856 |
| 6,176,142 B1 | * | 1/2001 | Ericson | 73/856 |
| 6,526,837 B1 | | 3/2003 | Grote et al. | |

(Continued)

FOREIGN PATENT DOCUMENTS

| | | |
|---|---|---|
| CN | 2294465 Y | 10/1998 |
| CN | 2612793 Y | 4/2004 |

(Continued)

OTHER PUBLICATIONS

ISR for PCT/US2010/025609 dated Oct. 24, 2011.

*Primary Examiner* — Max Noori
(74) *Attorney, Agent, or Firm* — Mark W. Croll; Paul F. Donovan

(57) ABSTRACT

The disclosure relates a safety shield for the jaws of a grip used for tensile or similar materials testing. The safety shield typically attached to the jaws and shields the jaws on two, three or four sides in order to reduce the hazard of a user placing his or her fingers between the jaws while positioning the testing sample or specimen therebetween. A user is typically able to adjust the position of the safety shield to achieve greater safety. The safety shield may be configured from planar material, such as sheet metal or plastic, or from wire material.

18 Claims, 3 Drawing Sheets

(56) References Cited

U.S. PATENT DOCUMENTS 7,475,892 B2 * 1/2009 Dudding et al. ......... 280/124.11
7,841,025 B1 * 11/2010 Fink et al. ........................ 2/414
7,884,598 B2 * 2/2011 Wang et al. .................... 324/127
8,201,463 B1 * 6/2012 Suhy et al. ............... 73/862.041

FOREIGN PATENT DOCUMENTS

| CN | 201107237 Y | 8/2008 |
| DE | 3537248 A1 | 4/1987 |
| DE | 102007008606 A1 | 3/2008 |

* cited by examiner

GRIP MOUNTED SAFETY SHIELD

BACKGROUND OF THE INVENTION

This application is national phase of PCT/US2010/025609 filed Feb. 26, 2010, and claims priority under 35 U.S.C. §119(e) of U.S. provisional application Ser. No. 61/165,207 filed Mar. 31, 2009.

FIELD OF THE DISCLOSURE

The present disclosure pertains to a shield for the jaws of a tensile testing or similar device, to reduce the possibility of injury to the user when inserting a specimen between the jaws of the device.

DESCRIPTION OF THE PRIOR ART

In materials testing, the specimen or testing sample is typically gripped and then pulled or compressed in order to measure the material properties of the specimen. The gripping mechanism can be of several types, including the automatic side-action grip, which can be pneumatic or hydraulic. Typically, the user holds the ends of the specimen between the jaws of the grip and then actuates a switch, typically by the user's hand or foot, to cause the jaws to come together and to grip the specimen. The closing of the jaws is often fast and with enough force that, should the user's fingertips be between the jaws, the user can receive a severe pinch injury. This hazard increases as the jaw face opening increases because this allows more space for a user to insert a finger between the jaws. Industry practice with respect to grips with large jaw face openings is to slow the grip closing speed enough to allow sufficient time for the user to withdraw the finger. However, the slowing of the speed of the jaw face slows the productivity of the user.

While certain safety shields have been common in the design of such devices as reciprocating saws and jig saws, it has been challenging to provide a simple shield that provides real safety for a materials testing device while not hindering user productivity. Indeed, the user must feel that the shield is providing or improving productivity or they may be tempted to defeat or remove the shield.

OBJECTS AND SUMMARY OF THE DISCLOSURE

It is therefore an object of the present disclosure to provide a safety shield for the jaws of a materials testing or similar device which reduces the risk of a pinch accident to the user while not impeding productivity.

This and other objects are obtained by providing a shield that is placed around the jaw face, covering two, three or four sides of the jaw face. The shield typically can be placed in the front or on the rear of the grip with respect to the user's position. The shield may further be adjusted to close down the opening to be large enough for the specimen to be inserted but not large enough for the user to insert their finger. The shield may remain fixed during operation of the grip and has markings and notches that can be used to align various types and sizes of specimens. Different shield sizes may be made available for different jaw face sizes. The shield may be placed close to the jaw face and surround the sides of the jaw face while being sized and shaped such that the user has some visibility as to the position of the jaw face and the position of the specimen with respect to the jaw face. With some materials testing devices, particularly those in which the jaw face is inserted and removed from one direction, the shield can typically be left in place while the user changes jaw faces.

BRIEF DESCRIPTION OF THE DRAWINGS

Further objects and advantages of the disclosure will become apparent from the following description and from the accompanying drawings, wherein.

DETAILED DESCRIPTION OF THE PREFERRED EMBODIMENTS

Figure 2:
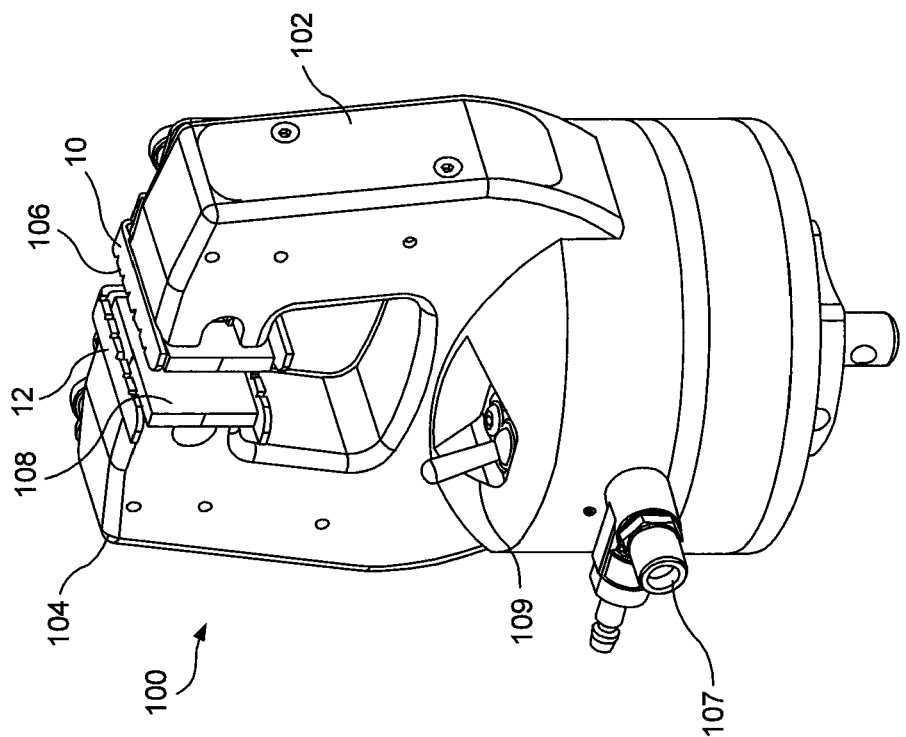
FIG. 2 is a rear perspective view of the first embodiment of the shield of the present disclosure, mounted on a jaw device.
Figure 1:
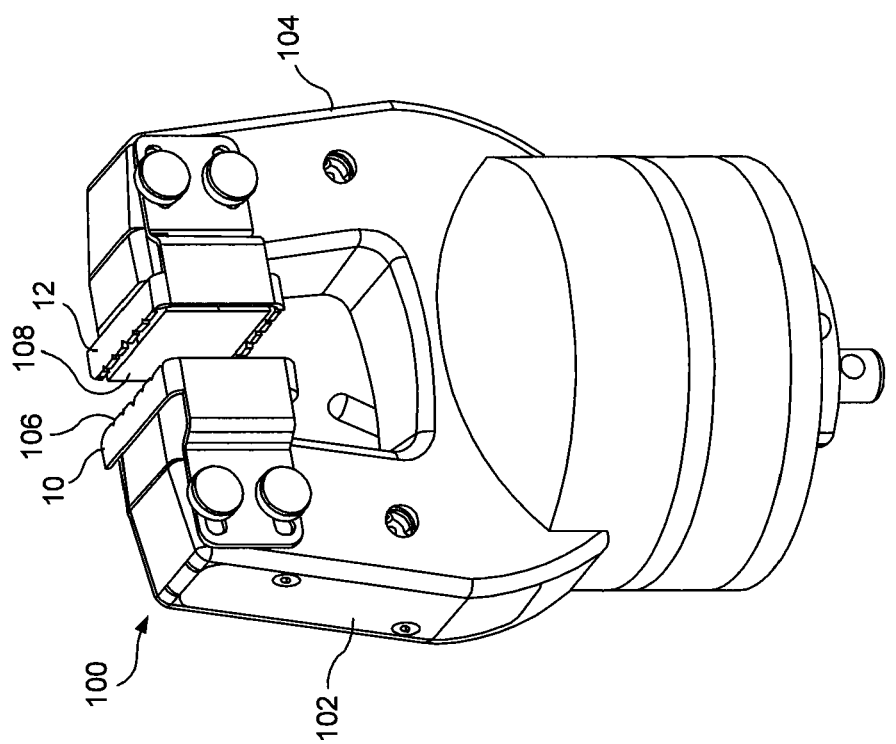
FIG. 1 is a front perspective view of a first embodiment of the shield of the present disclosure, mounted on a jaw device.
Figure 3:
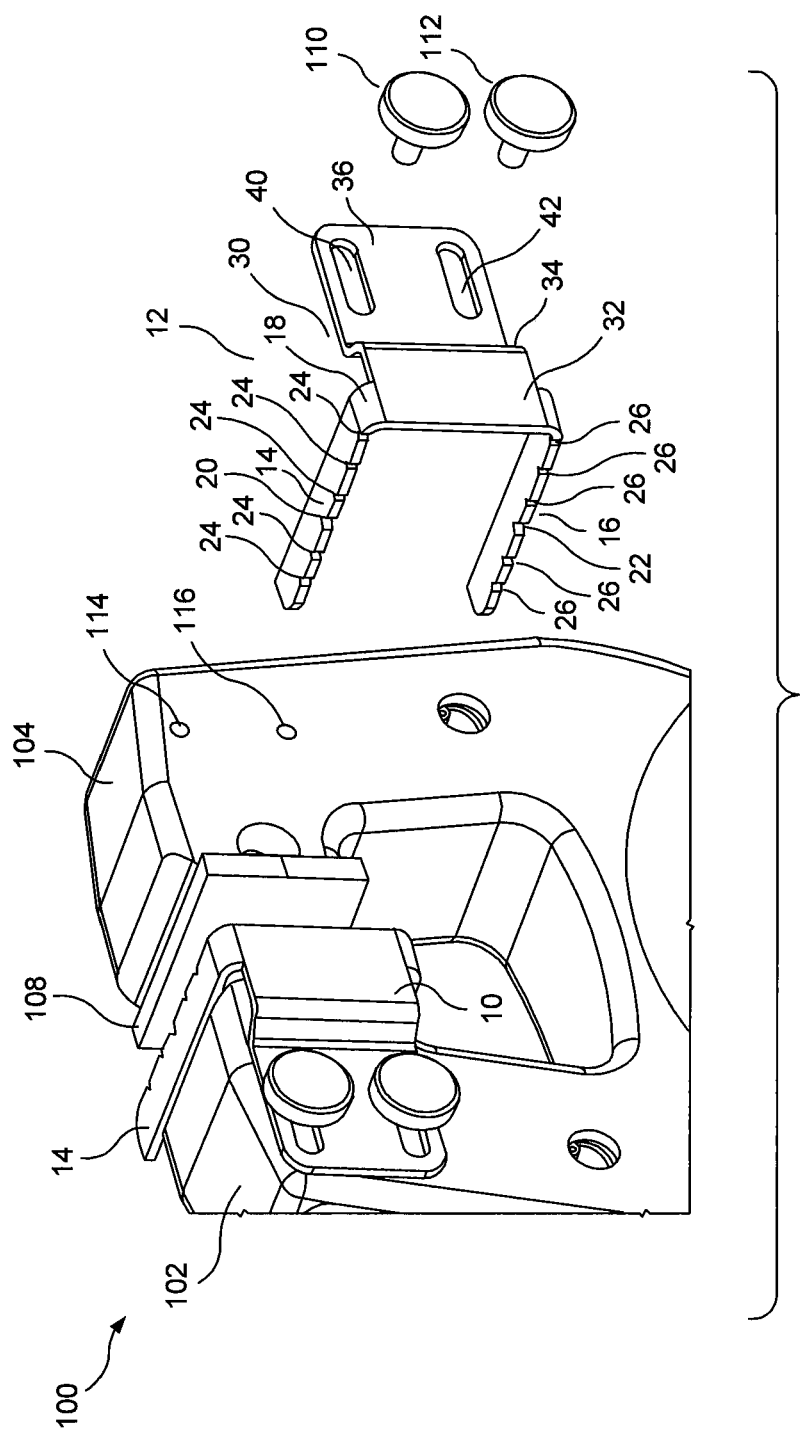
FIG. 3 is an exploded perspective view of the first embodiment of the shield of the present disclosure, mounted on a jaw device.

Referring now to the drawings in detail wherein like numerals indicate like elements throughout the several views, one sees that FIGS. 1-3 illustrate a grip 100 such as is used in materials testing, with a first embodiment of first and second safety shields 10, 12. Grip 100 includes first and second jaws 102, 104 with opposed first and second jaw faces 106, 108 which reciprocate toward and away from each other. As is known in the prior art, first and second jaw faces 106, 108 grip a tensile material testing sample or specimen (not shown) and, in combination with a similar opposed grip, typically pull or compress the sample in a direction parallel to the first and second jaw faces 106, 108. FIG. 2 illustrates the pneumatic or hydraulic port 107 and the control switch 109 of the grip 100.

First and second safety shields 10, 12 are mounted on respective first and second jaws 102, 104 with a view to preventing the user's fingers from entering between first and second jaw faces 106, 108 when the testing sample is first inserted and as first and second jaw faces 106, 108 are thereafter brought together. The illustrated embodiments of first and second safety shields 10, 12 can be symmetric to the extent that they may be manufactured to be identical to each other, and then flipped or turned as necessary to provide the mirror-image configuration shown in FIG. 3. First and second safety shields 10, 12 are typically formed from sheet metal, plastic or wire, but those skilled in the art will recognize a range of equivalents after review of this disclosure.

Safety shields 10, 12 each include upper and lower horizontal safety arms 14, 16 joined in a U-shaped configuration with a vertical connector 18 therebetween. Vertical connector 18 likewise serves as a front safety shield. Upper and lower horizontal safety arms 14, 16 and vertical connector 18 are intended to shield the user from placing his or her fingers between the first and second jaws 102, 104 from the top, bottom or front. While not shown, a second vertical connector could attach the tips of the upper and lower horizontal safety arms 14, 16 thereby shielding the rear of the first and second jaws 102, 104. Upper and lower safety arms 14, 16 include respective central notches 20, 22 to allow the user to quickly center a testing sample in the shape of a wire, string or small tube in the grip opening. While a notch may be used in order to provide a measure of tactile feel to the user for determining if the testing sample is in the correct position before activating the grip 100, other embodiments may use central marks in lieu of central notches 20, 22. Additional notches 24, 26 (or marks) are likewise placed at periodic locations along upper and lower safety arms 14, 16 in order to provide additional visibility and flexibility to the user with respect to the placement of the testing sample.

Flange 30 with a proximal portion 32 and a distal portion 36 is secured to vertical connector 18. Flange 30 typically includes ridge 34 between proximal portion 32 and distal portion 36 so that the interior surface of distal portion 36 is coplanar with the interior surface of vertical connector 18 so that distal portion 36 can engage or lie flat against the respective jaw. Distal portion 36 includes parallel slots 40, 42 through which thumbscrews 110, 112 extend and threadably attach to threaded apertures 114, 116 in first and second jaws 102, 104 (hidden from view on first jaw 102) thereby fastening the first and second safety shields 10, 12 to the sides of first and second jaws 102, 104. This configuration allows for the adjustment throughout a range of horizontal positions of the first and second safety shields 10, 12 by the user in order to achieve greater safety for the specific application. Thumbscrews 110, 112 may be separate parts or made captive within parallel slots 40, 42.

Figure 4:
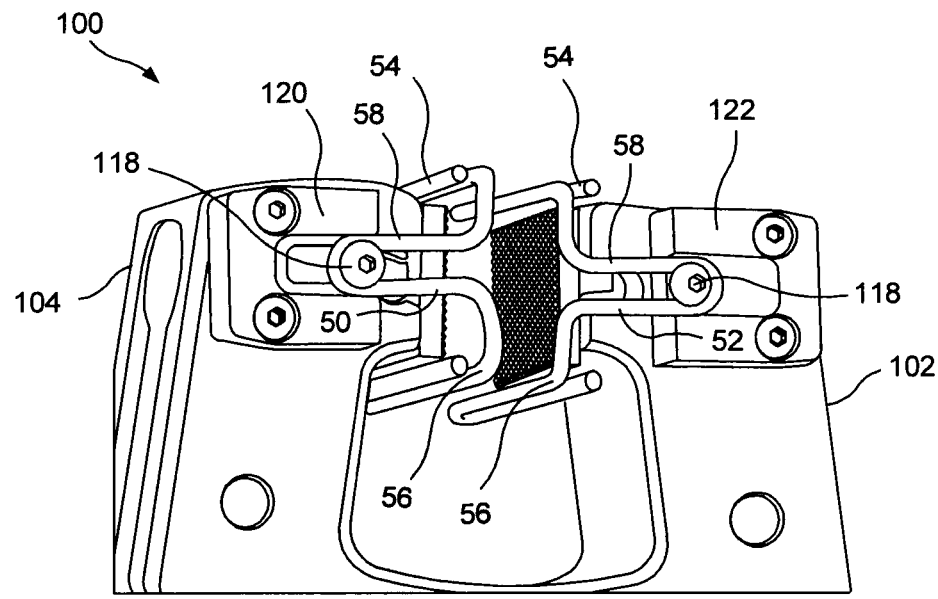
FIG. 4 is a front perspective view of a second embodiment of the shield of the present disclosure, mounted on a jaw device.
Figure 5:
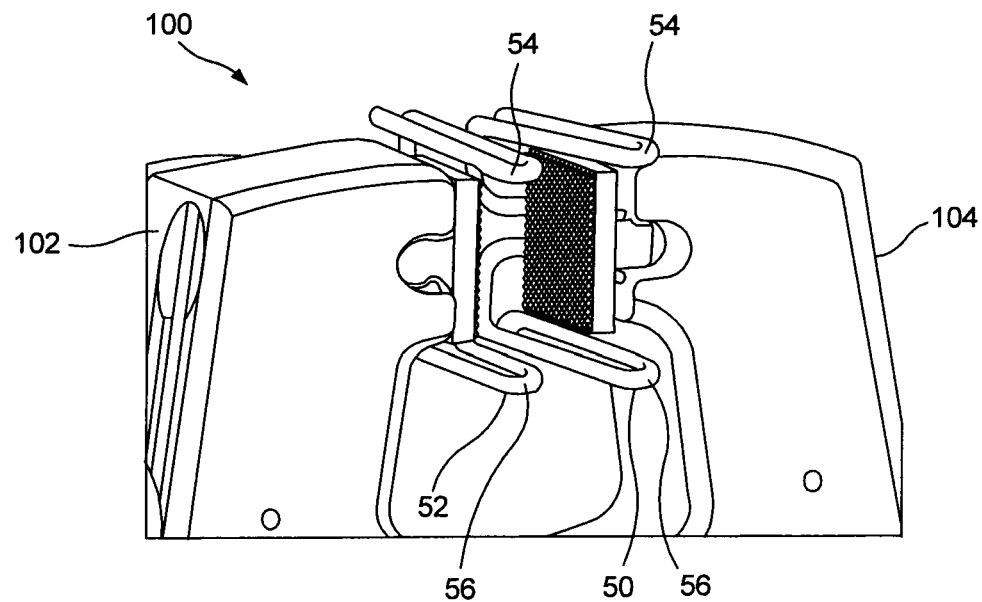
FIG. 5 is a rear perspective view of the second embodiment of the shield of the present disclosure, mounted on a jaw device.

A second embodiment is illustrated in FIGS. 4 and 5. First and second safety shields 50, 52 are formed from a length of wire which is shaped to cover two or three sides of the first and second jaw faces 106, 108. Each safety shield 50, 52 is typically formed from a single continuous length of metal wire. Top and bottom horizontal bent-back portions (or loops) 54, 56 form respective upper and lower shields. Top and bottom horizontal bent-back portions 54, 56 include two sections of wire oriented substantially parallel to each other and joined by a sharp bend. Top and bottom horizontal bent-back portions 54, 56 are joined to each other by central vertical bent-back portion (or loop) 58 which is configured and arranged to receive screw 118 to mount the first and second safety shields 50, 52 on respective first and second mounting surfaces 120, 122 on the respective first and second jaws 102, 104. The first and second mounting surfaces 120, 122 include a threaded aperture (not shown) to receive screw 118 and may be part of or integral with the first and second jaws 102, 104 or may be separate pieces attached thereto.

To use either embodiment of the present disclosure, the user places first and second safety shields 10, 12 or 50, 52 on respective first and second jaws 102, 104 and adjusts the position so as to provide maximum safety in blocking access of the user's fingers to the space between the first and second jaw faces 106, 108. The user then fixes the position of safety shield 10, 12 or 50, 52 by tightening screws 110, 112 or 118. The user is then ready to commence tensile or similar material testing.

Thus the several aforementioned objects and advantages are most effectively attained. Although preferred embodiments of the invention have been disclosed and described in detail herein, it should be understood that this invention is in no sense limited thereby and its scope is to be determined by that of the appended claims.

What is claimed is:

1. A shield for a jaw of a reciprocating grip, including:
a top shield portion for positioning over the jaw;
a bottom shield portion for positioning under the jaw;
a connector portion connecting the top shield portion to the bottom shield portion; and
a fastening portion for fastening the shield to the jaw, the fastening portion comprising a flange with a proximal portion attached to the connector portion and a distal portion which engages against the jaw.

2. The shield of claim 1 wherein the fastening portion allows the shield to be fastened to the jaw throughout a range of positions.

3. The shield of claim 1 wherein the distal portion includes at least one slot, wherein a user can place a screw through the at least one slot and into a threaded aperture in the jaw.

4. The shield of claim 3 wherein the distal portion includes two parallel slots, wherein a user can place screws through the two parallel slots and into threaded apertures in the jaw.

5. The shield of claim 4 wherein a ridge is formed between the proximal portion and the distal portion of the flange.

6. The shield of claim 5 wherein the connector portion forms a front shield portion.

7. The shield of claim 2 wherein at least one of the upper and lower shield portions include a central notch or mark.

8. The shield of claim 7 wherein at least one of the upper and lower shield portions includes a plurality of notches or marks along the length thereof.

9. The shield of claim 1, wherein the shield is formed from metal.

10. The shield of claim 1, wherein the shield is formed from plastic.

11. The shield of claim 1, wherein the shield is symmetric so that it can be flipped to form a mirror image of itself.

12. A shield for a jaw of a reciprocating grip, including:
a top shield portion formed from a first portion of wire for positioning over the jaw;
a bottom shield portion formed from a second portion of wire for positioning under the jaw;
a connector portion formed from a third portion of wire connecting the top shield portion to the bottom shield portion; and
a fastening portion for fastening the shield to the jaw.

13. The shield of claim 12 wherein the first, second and third portions of wire are formed from a single piece of wire.

14. The shield of claim 13 wherein the single piece of wire is formed continuously.

15. The shield of claim 14 wherein the single piece of wire is formed from metal.

16. The shield of claim 15 wherein the first and second portion of wire are each formed from two substantially parallel sections of wire joined by a bend therebetween.

17. The shield of claim 16 wherein the connector portion includes a portion for receiving a screw therethrough.

18. The shield of claim 17 wherein the connector portion serves as a front shield portion.

* * * * *